(12) United States Patent
Yeary

(10) Patent No.: US 11,771,844 B2
(45) Date of Patent: Oct. 3, 2023

(54) SYRINGE DE-CAPPER DEVICE

(71) Applicant: AMGEN INC., Thousand Oaks, CA (US)

(72) Inventor: Jeffrey C. Yeary, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 17/685,433

(22) Filed: Mar. 3, 2022

(65) Prior Publication Data

US 2022/0313924 A1 Oct. 6, 2022

Related U.S. Application Data

(60) Provisional application No. 63/168,098, filed on Mar. 30, 2021.

(51) Int. Cl.
*A61M 5/32* (2006.01)
*A61M 5/00* (2006.01)

(52) U.S. Cl.
CPC .......... *A61M 5/3204* (2013.01); *A61M 5/002* (2013.01)

(58) Field of Classification Search
CPC ............................ A61M 5/3204; A61M 5/002
USPC ................................. 206/366, 365, 570, 571
See application file for complete search history.

(56) References Cited

U.S. PATENT DOCUMENTS

| | | | | |
|---|---|---|---|---|
| 5,975,295 A | * | 11/1999 | Diamond | A61M 5/008 206/366 |
| 6,279,743 B1 | * | 8/2001 | Ballard | A61M 5/3204 211/70.6 |
| 2005/0171483 A1 | * | 8/2005 | Williams | A61M 5/3205 604/187 |
| 2012/0186075 A1 | * | 7/2012 | Edginton | A61M 5/2033 29/700 |
| 2012/0191048 A1 | * | 7/2012 | Eaton | A61M 5/46 604/198 |
| 2015/0359972 A1 | * | 12/2015 | Huang | A61M 5/3202 29/281.1 |
| 2019/0255256 A1 | * | 8/2019 | Holmqvist | A61M 5/31576 |
| 2020/0197622 A1 | * | 6/2020 | McLusky | A61M 5/3287 |

* cited by examiner

*Primary Examiner* — Jacob K Ackun
(74) *Attorney, Agent, or Firm* — MARSHALL, GERSTEIN & BORUN LLP; Michael P. Furmanek

(57) ABSTRACT

A syringe de-capper including a base having a lower surface and an upper surface opposite the lower surface. The syringe de-capper also includes a de-capping member extending from the upper surface of the base, the de-capping feature including a proximal end adjacent to the base, a distal end spaced away from the base. The de-capping feature includes opposing first and second lateral surfaces defining a proximal thickness at the proximal end and a distal thickness at the distal end, the distal thickness is smaller than the proximal thickness. Also, the syringe de-capper includes a slot disposed in the de-capping member, the slot extending from the distal end of the de-capping member toward the proximal end of the de-capping member and configured to slidably receive a distal end of a syringe for removing a cap therefrom.

20 Claims, 8 Drawing Sheets

SYRINGE DE-CAPPER DEVICE

CROSS-REFERENCE TO RELATED APPLICATION

Priority is claimed to U.S. Provisional Patent Application No. 63/168,098, filed Mar. 30, 2021, the entire contents of which are hereby expressly incorporated by reference herein.

FIELD OF DISCLOSURE

The present disclosure relates to syringe accessories and, more particularly, to syringe de-capping devices.

BACKGROUND

Syringes for medical uses typically include a syringe barrel, a needle, and a cap disposed over the needle. The needle of most syringes used in the medical industry are ultra-sharp and designed for puncturing drug vials and skin. As a result, the cap disposed over the needle is to both keep the needle sterile and also prevent accidental scratches and punctures with the needle. Accordingly, the cap is secured onto the needle and covers most of the needle until the cap is removed by a medical practitioner, researcher, or patient, for example. After the cap is removed, the syringe can be used by the medical practitioner, researcher, or patient.

When removing the cap, the needle can accidentally scratch or stick the syringe user. As a result, de-capping can be a dangerous activity for syringe users. And many syringe users, such as medical practitioners and researches, are required to de-cap a large number of syringes in the course of their work. Safely de-capping a syringe can be a time consuming process that requires good hand dexterity and strength. With typical syringe de-capping methods, syringe users can struggle de-capping syringes either because they need to work quickly or lack good hand strength and dexterity.

SUMMARY

Disclosed herein is a syringe de-capper including a base having a lower surface and an upper surface opposite the lower surface. The syringe de-capper also includes a de-capping member extending from the upper surface of the base, the de-capping feature including a proximal end adjacent to the base, a distal end spaced away from the base. The de-capping feature includes opposing first and second lateral surfaces defining a proximal thickness at the proximal end and a distal thickness at the distal end, the distal thickness is smaller than the proximal thickness. Also, the syringe de-capper includes a slot disposed in the de-capping member, the slot extending from the distal end of the de-capping member toward the proximal end of the de-capping member and configured to slidably receive a distal end of a syringe for removing a cap therefrom.

Also disclosed herein is a syringe storage and de-capper kit including a container having an interior cavity and a removable lid. The syringe storage and de-capper kit includes a syringe disposed within the container having a removable cap disposed over a needle extending from a distal end of the syringe; and a syringe de-capper configured to de-cap the syringe, including a de-capping member extending from a base, the de-capping member including a proximal end adjacent to the base, a distal end spaced away from the base, and opposing first and second lateral surfaces defining a proximal thickness at the proximal end and a distal thickness at the distal end, wherein the distal thickness is smaller than the proximal thickness.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicated of the presence or absence of particular elements in any of the exemplary embodiments, except as may be explicitly delineated in the corresponding written description. Also, none of the drawings are necessarily to scale

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercial feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Typical syringe de-capping requires good hand strength and dexterity, but poses a risk to the user. While syringe de-capping apparatus reduces the hand strength required to de-cap a syringe, the risks of de-capping a syringe are still possible. Further, current apparatus that are designed to improve the syringe de-capping process often require forcing the syringe cap into a larger cap that is easier to hold, but forces the cap further onto the syringe. As a result, connecting the typical syringe de-capping apparatus makes pulling the cap off the syringe more difficult.

In accordance with the present disclosure, the syringe de-capper allows a user to de-cap most syringes with one hand, reduced hand strength, and reduced hand dexterity. The syringe de-capper includes at least one slot configured to de-cap a syringe. For example, the slot has a width smaller than a barrel of the syringe and the cap, but larger than a needle or needle hub. When the syringe de-capper is disposed between the syringe barrel and the syringe cap, the user can push the syringe downwards. As the syringe is pushed downwards, the cap is spaced apart from the syringe barrel by the syringe de-capper until the cap is no longer disposed on the needle.

Figure 1:
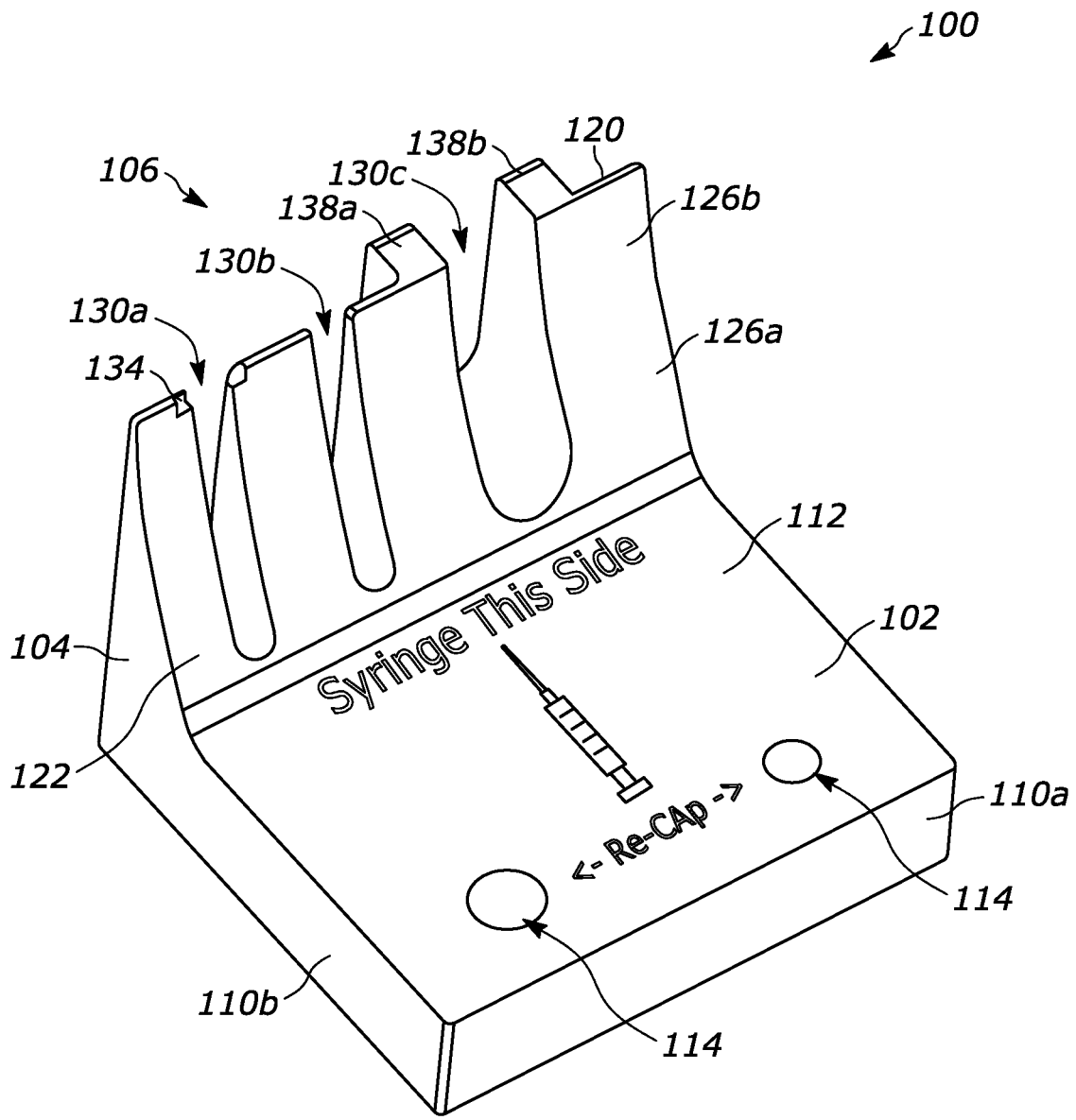
FIG. 1 is a perspective view of a syringe de-capper of the present disclosure.
Figure 2:
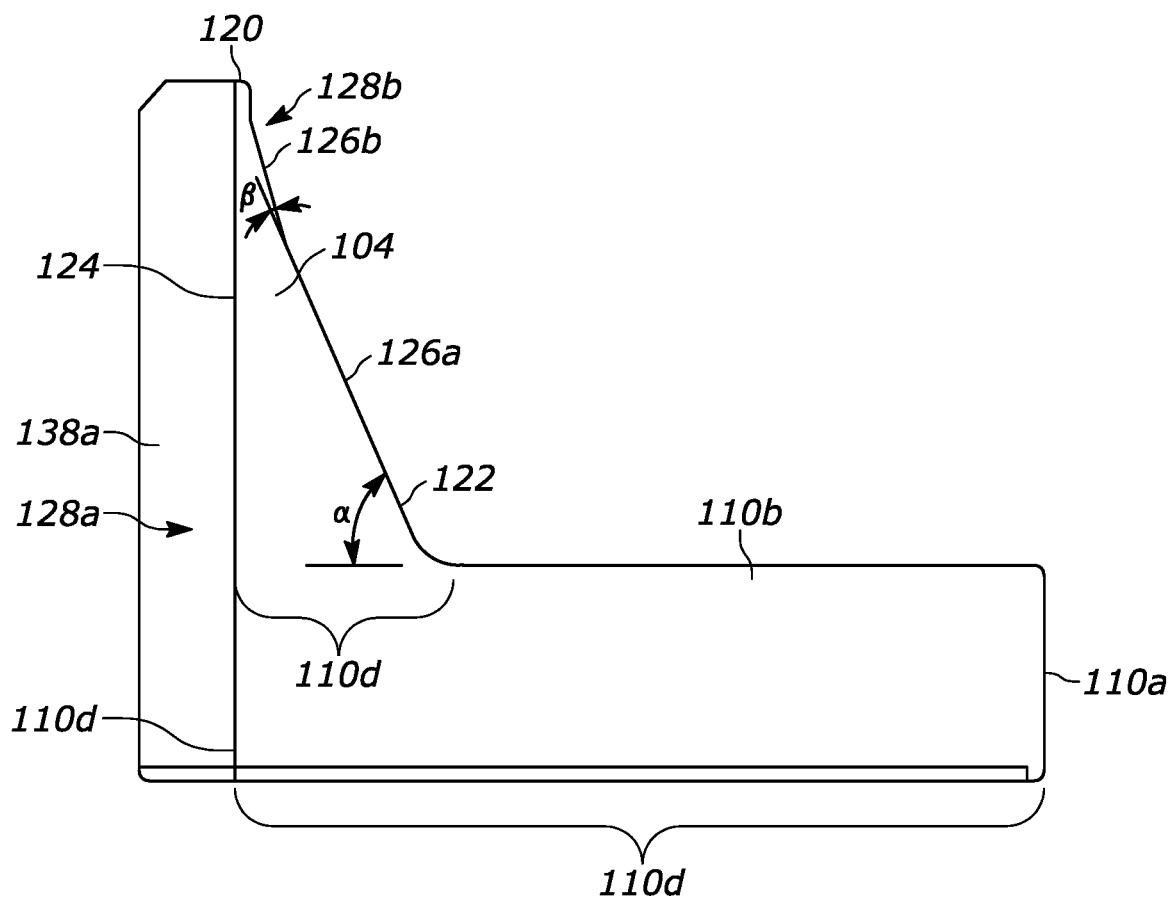
FIG. 2 is a side view of the syringe de-capper of FIG. 1.
Figure 3:
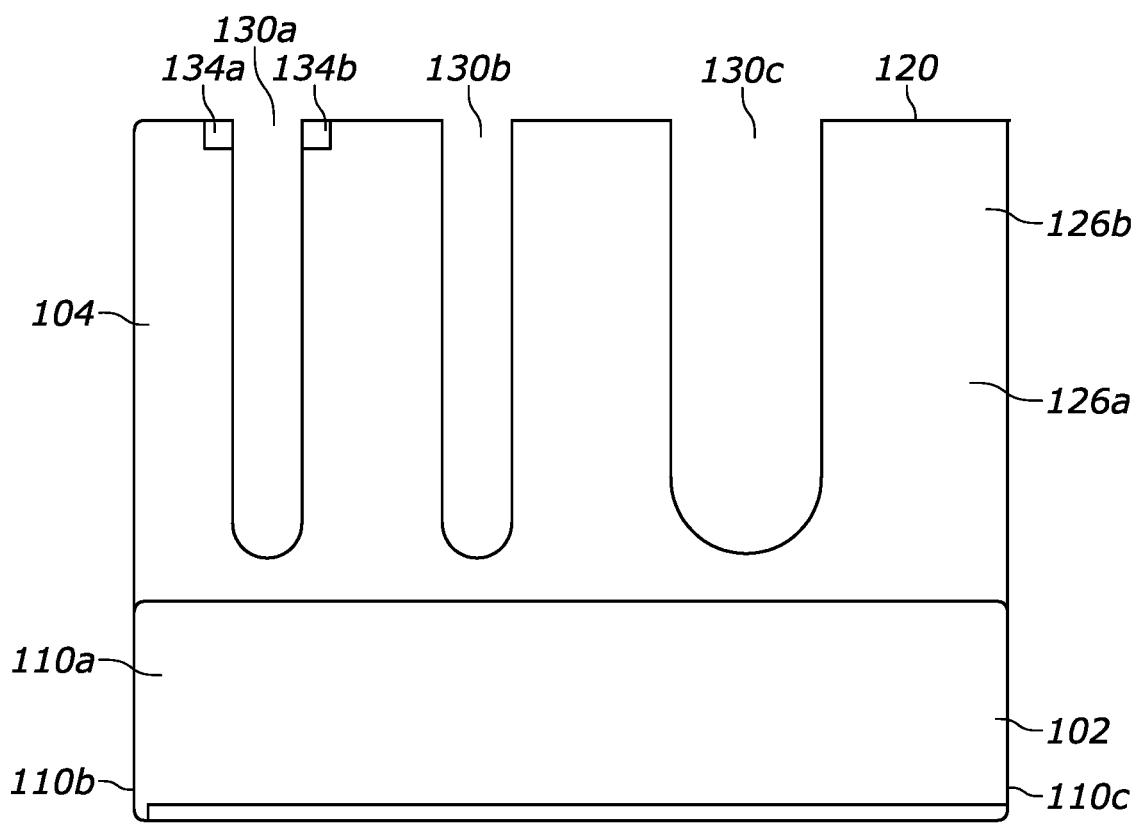
FIG. 3 is a front view of the syringe de-capper of FIG. 1.

FIGS. 1, 2, and 3 illustrate an example syringe de-capper 100 of the present disclosure. The syringe de-capper 100 includes a base 102, a de-capping member 104, and a plurality of slots 106. As shown in the figure, the de-capping member 104 extends generally upward or vertically from one end of the base 102. However, in other embodiments, the de-capping member 104 can be disposed centrally on the base 102 or the base 102 can be disposed entirely underneath the de-capping member 104. Furthermore, the de-capping member 104 is shown integrally formed with the base 102, however, in some examples, the de-capping member 104 can be removably attached with the base 102.

The base 102 includes a front wall 110a, a first sidewall 110b, a second sidewall 110c, and a rear wall 110d. Additionally, the base 102 also includes an upper surface 112 disposed between the front wall 110a, the first sidewall 110b, and the second sidewall 110c. The upper surface 112 can be a smooth surface, can include instructions for use, can include warnings, or a combination of instructions and warnings. In some examples, the base 102 includes one or more apertures 114 in the upper surface 112 of the base 102 configured to receive the cap of the syringe. Any aperture 114 in the upper surface 112 is provided for re-capping a needle after the syringe has been used. In some examples, the aperture(s) 114 is configured to loosely hold a needle cap. The base 102 can additionally be designed for comfortable handheld movement and control. For example, the width of the base between the first sidewall 110b and the second sidewall 110c can be between approximately 0.5 inches and 6 inches. Additionally, the height of the base 102 can be between approximately 0.25 inches and 1.5 inches. As a result, the syringe de-capper 100 is easily moved and manipulated by a user.

As illustrated in FIGS. 1, 2, and 3, the de-capping member 104 is integrally attached with the base 102. The de-capping member 104 includes an edge 120 disposed between a first surface 122 and a second surface 124 (seen in FIG. 2). The edge 120 is disposed at a distal end of the de-capping member 104, relative the base 102. Additionally, the first surface 122 and the second surface 124 diverge from the edge 120 to form a generally wedge-shaped de-capping member 104. The edge 120 can be a flat surface, a sharp or dull pointed edge, a partially rounded surface, or any other suitable shape and configuration. For example, the edge 120 can include a quarter circle or semicircle with a radius between approximately 0.02 inches and approximately 0.1 inches.

Additionally, the first surface 122 and the second surface 124 form the generally wedge-shaped de-capping member 104. The second surface 124 in the disclosed embodiment, as shown, extends generally perpendicular (e.g., 90 degrees) to the base 102. In contrast, the first surface 122 is angled other than 90 degrees relative the base 102 and the second surface 124. Further, the first surface 122 may include a plurality of wall portions having different angles relative the base 102. For example, the first surface 122 may include a first wall portion 126a adjacent the base 102 having a first angle $\alpha$ between approximately 30 degrees and approximately 75 degrees relative the upper surface 112. Additionally, adjacent the first wall portion 126a, a second wall portion 126b can define a second angle, adding an additional approximately 5 degrees to approximately 20 degrees to the first angle, relative the upper surface 112. As a result, the angle $\beta$ of the second wall surface is between approximately 35 degrees and approximately 85 degrees, relative the upper surface 112. In other examples, the first surface 122 provides a continuously variable angle between the upper surface 112 and the edge 120, providing a smooth transition of increasing angle between the upper surface 112 and the edge 120. In other examples, the first surface 122 may be perpendicular with the upper surface 112 and the second surface 124 may be angled other than 90 degrees relative the upper surface 112, or both the first surface 122 and the second surface 124 can be angled other than 90 degrees relative the upper surface 112. In yet another version it is conceivable that at least some portion of the de-capping member 104 can include a thin wall of generally uniform width having both the first surface and the second surface 124 disposed perpendicular to the upper surface 112. So configured, to remove the cap, the user may have to pull the syringe away from the de-capping member 104 and the cap against second surface 124 after positioning the de-capping member 104 between the barrel and the cap. In some such configurations, portions of the first and second surfaces of the de-capping member 104 may also define a sharp divergent knife edge for facilitating alignment of the de-capping member between the barrel and the cap. In still other versions, the divergent first and second surfaces 122, 124 need not be planar surfaces but rather can include curved, concave, convex, a combination of concave and convex, and/or any other shaped surfaces suitable for the intended purpose of the disclosure.

As shown, the generally wedge-shaped de-capping member 104 includes a proximal end 128a that is thicker than the distal end 128b, e.g., the edge 120. In some examples, the proximal end, or a base of the de-capping member, has a thickness of between approximately 0.5 inches and approximately 1.25 inches. Additionally, the edge 120 can have a thickness of approximately 0.02 inches to approximately 0.1 inches. In some examples, the thickness of the de-capping member at the base is greater in magnitude than the length of the syringe needle. The base 102 has a base footprint 129a and the de-capping member 104 has a de-capping footprint 129b. As shown, the base footprint 129a is larger than the de-capping footprint 129b, however in some examples, the de-capping footprint 129b is the same as the base footprint 129a.

The de-capping member 104 additionally includes a plurality of slots 106. For example, as shown in FIG. 1, the de-capping member of the present example includes three slots, i.e., a first slot 130a, a second slot 130b, and a third slot 130c. While the disclosed version includes three slots, in other versions, the de-capping member 104 can have less than or more than three slots. In the disclosed version, the first slot 130a and the second slot 130b are approximately the same width (between approximately 0.15 inches and approximately 0.3 inches) and the third slot 130c has a wider width (between approximately 0.3 inches and approximately 0.65 inches). The width of each of the plurality of slots 106 is configured to receive a needle, or needle hub of a syringe, but not receive the syringe barrel or the cap of the syringe. As a result, a user can pass the needle and needle hub down one of the plurality of slots 106. As the needle and needle hub are pressed down, the syringe barrel and needle cap are separated by the de-capping member 104, thereby removing the needle cap because the de-capping member 104 becomes thicker as the needle moves towards the base 102.

The first slot 130a additionally includes a recesses 134a and 134b disposed in the edge 120 of the de-capping member 104. The recesses 134a and 134b are disposed in the edge 120 of the de-capping member 104 and adjacent the slot 130a. The recesses 134a and 134b further reduce a thickness of the edge 120. In some examples, the thickness of the edge 120 is reduced to approximately 0.01 to approximately 0.05 inches. As a result, the de-capping member 104 can fit between the syringe barrel and the needle cap even if the syringe barrel and needle cap are manufactured with a minimal gap. In contrast, the de-capping member 104 also includes ribs 138a and 138b disposed on either side of third slot 130c. The ribs 138a and 138b increase the thickness of the de-capping member 104, to accommodate larger syringes that include longer needles and bigger gaps between the syringe barrel and the needle cap. The ribs 138a and 138b can increase the thickness of the de-capping member between approximately 0.25 inches and approximately 0.5 inches. As a result, the edge, in conjunction with the rib, can have a thickness between approximately 0.27 and approximately 0.6 inches.

Figure 4:
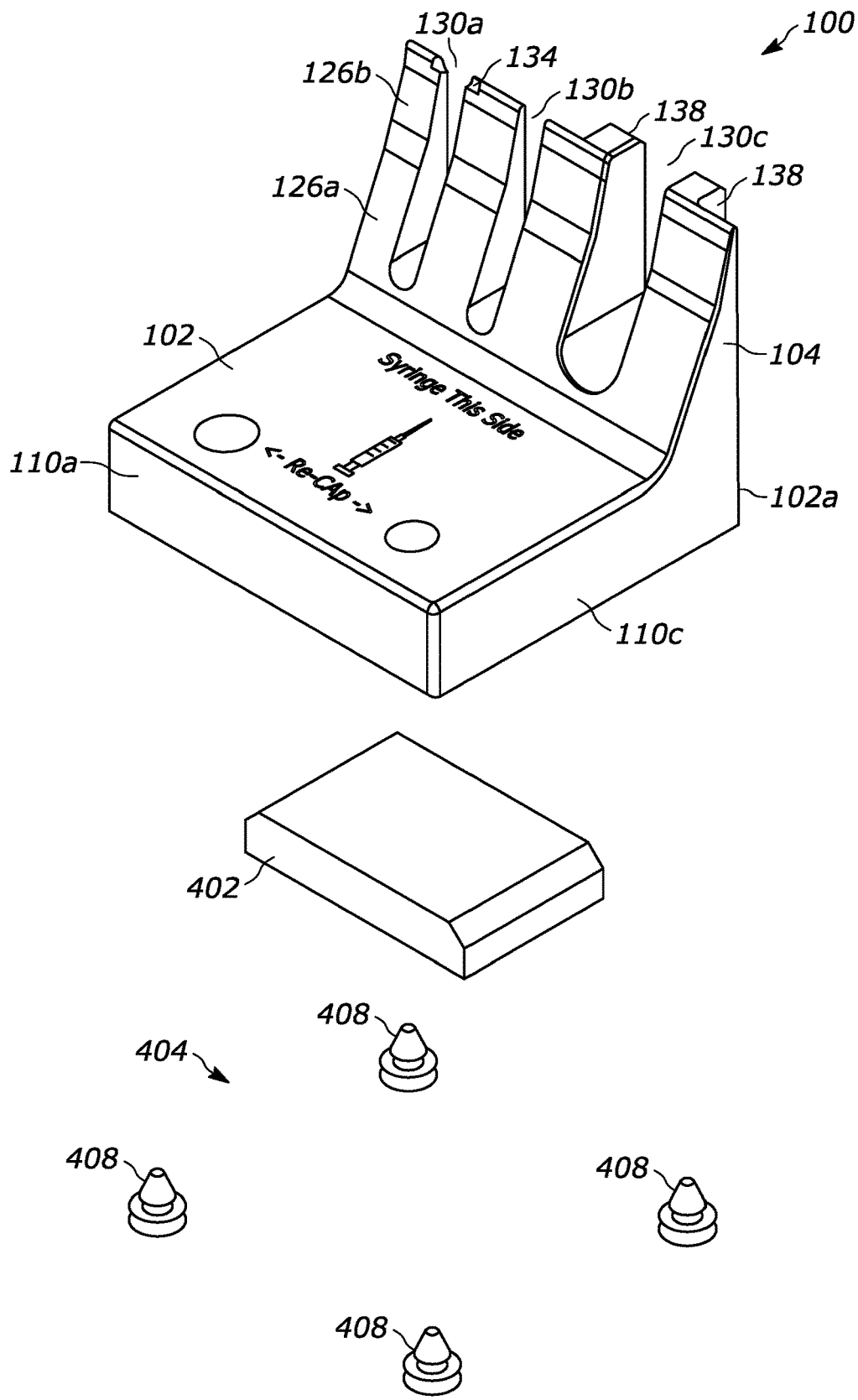
FIG. 4 is a perspective view of the syringe de-capper of FIG. 1 in an exploded view.

FIG. 4 is a perspective view of the syringe de-capper of FIG. 1 in an exploded view. The syringe de-capper 100 includes a weight 402 and a non-slip interface 404. In accordance with the teachings of the present disclosure, the weight 402 and non-slip interface 404 assist in stabilizing the syringe de-capper on a table or lab workbench. As shown in FIG. 4, the non-slip interface 404 includes four rubber feet 408. In alternative examples, the rubber feet 408 could be replaced with an alternative non-slip interface 404, such as a non-slip pad or coating disposed on the bottom of the base 102. Furthermore, the weight 402 and the non-slip interface 404 can be replaced with a suction cup coupled to a lower surface of the base 102 and configured to secure and stabilize the syringe de-capper 100 to a table or lab workbench.

Figure 5A:
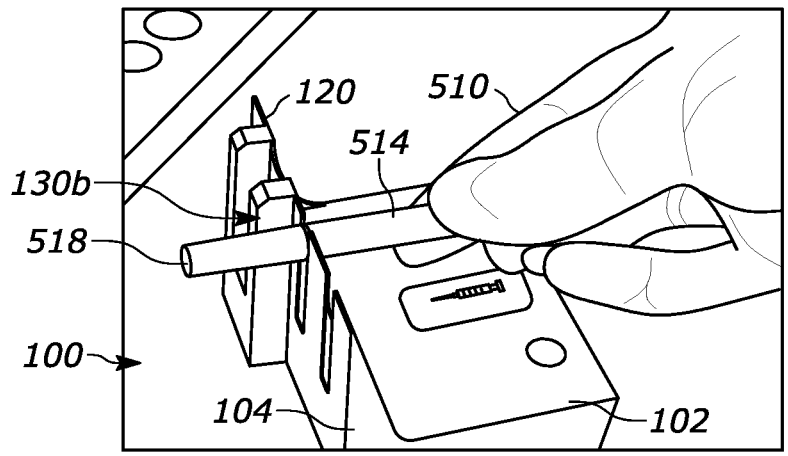
FIGS. 5A, 5B, and 5C are perspective views of the syringe de-capper of the present disclosure used to de-cap a syringe.
Figure 5B:
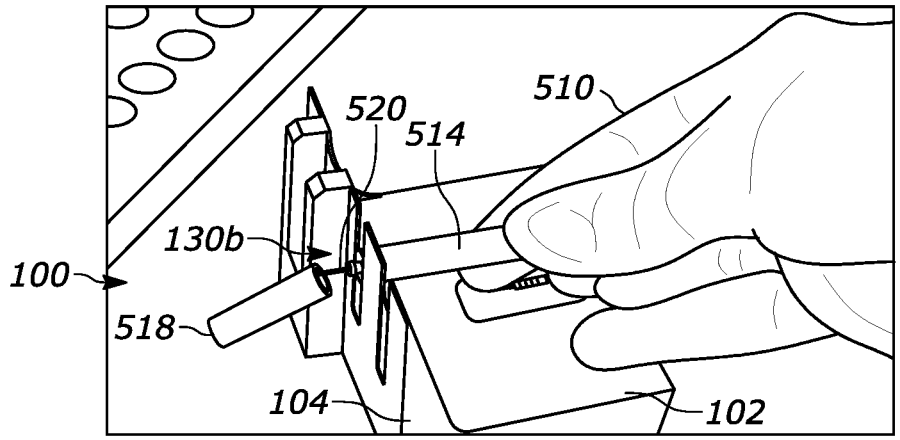
Figure 5C:
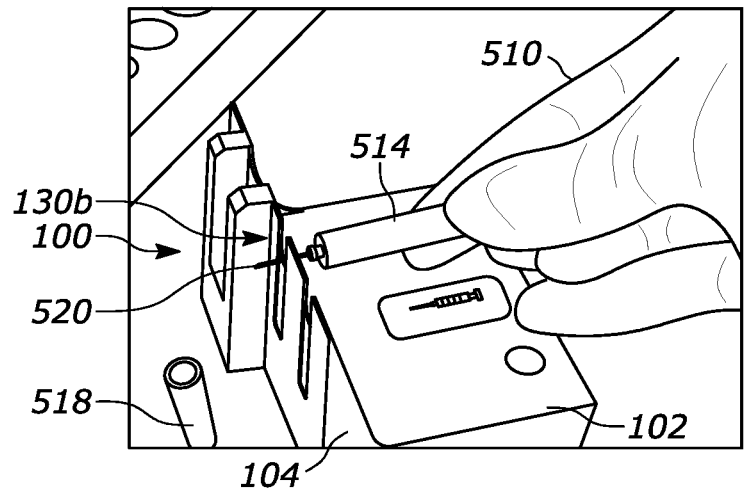

FIGS. 5A, 5B, and 5C provide an example method of using the syringe de-capper 100 of the present disclosure to de-cap a syringe. As shown in the figures, a person 510 is shown using the syringe de-capper 100 of FIGS. 1-3 to de-cap a syringe 514 having a cap 518 with a single hand. As an initial step, the person 510 places the barrel of the syringe 514 on the slot 514 and pulls the syringe 514 towards the front wall 110 until the edge 120 slides into a gap or interface disposed between the syringe 514 and the cap 518.

Subsequently, after the edge 120 slides between the syringe 514 and the cap 518, the person 510 pushes the syringe 514 down towards the base 102. As the person 510 pushes the syringe 514 down towards the base 102, the syringe 514 slides along the first surface 122 while the cap 518 slides along the second surface 124. As a result, as the syringe 514 approaches the base 102, the diverging geometry of the de-capping member 120 causes the syringe 514 and the cap 518 separate. As the syringe 514 and the cap 518 separate, a needle 520 becomes exposed and visible. The person continues to push the syringe 514 towards the base 102 of the syringe de-capper 100 until the cap 518 falls off the needle 520, as shown in FIG. 5C. After the cap 520 falls away from the needle 520, the person can pull the syringe 514 out of the slot 130b and use the syringe 514. As shown in FIGS. 5A, 5B, and 5C, the person 510 was able to de-cap the syringe 514 using a single hand and without requiring much hand strength or dexterity. Additionally, the person's hand is always located away from the needle end of the syringe, protected against any accidental needle sticks or scratches from the needle.

Further, when re-capping, the person 510 places the cap 518 in one of the apertures 114. The cap 518 is loosely held within the aperture 114 such that the cap 518 can be placed into and removed from the aperture 114 without significant force. That is, in some versions, the cap 518 is not frictionally held within the aperture 114. In other examples, the cap 518 needs to be pushed into the aperture 114 and there is some amount of friction to retain the cap 518. With the cap 518 disposed in the aperture, the user is able to lower the syringe 514 and the needle 520 into the cap 518. Because the cap 518 is gravitationally positioned in the aperture 114, the syringe 518 can be easily re-capped with downward force applied with one hand. Additionally, because the person 510 only needs to use one hand, this re-capping process advantageously minimizes any chance for needle sticks. That is, because the base 102 instead of the person's other hand is holding the cap 518, any misalignment between the needle and the cap 518 during re-capping can only result in the needle sticking the base 102, which is of no concern.

Figure 6:
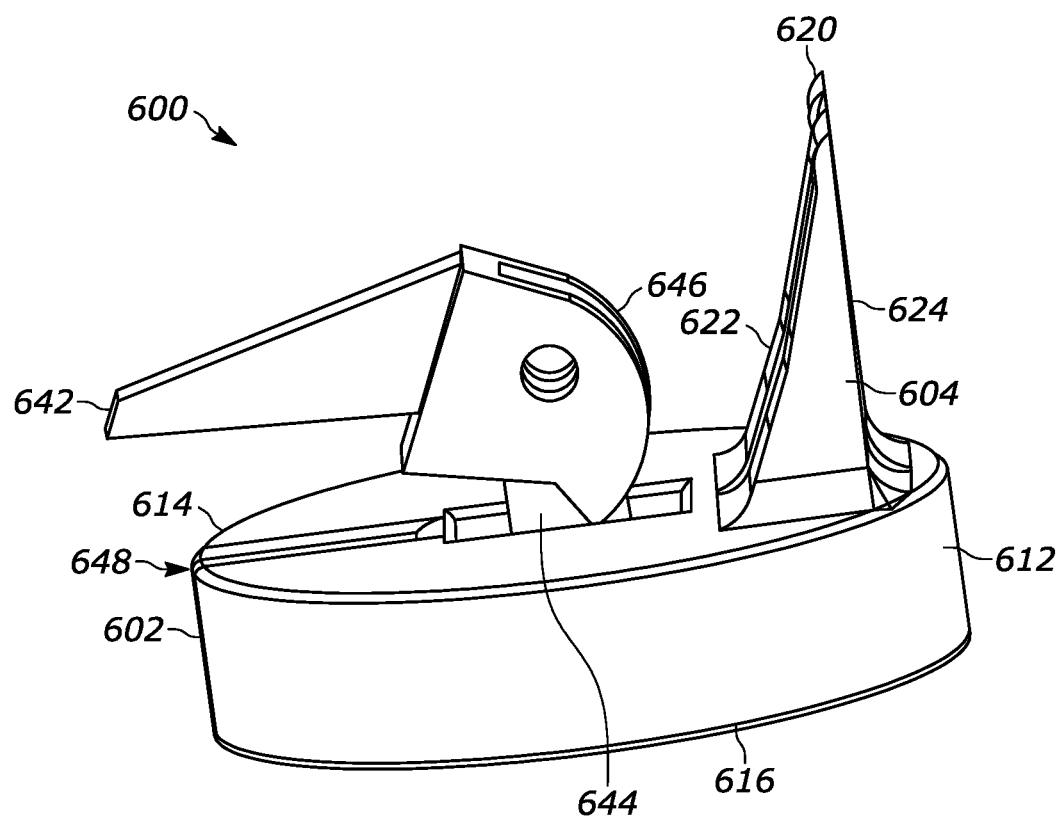
FIG. 6 is a side view of an alternative syringe de-capper of the present disclosure.
Figure 7:
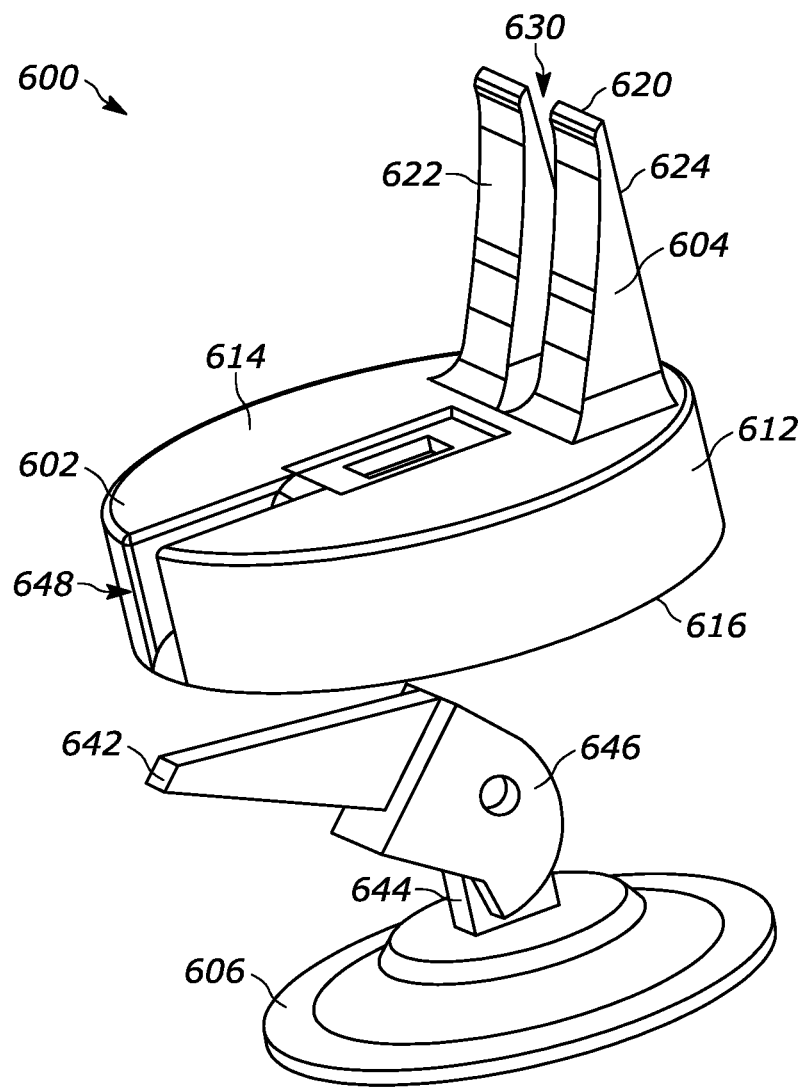
FIG. 7 is a perspective view of the alternative syringe de-capper of the present disclosure in an exploded view.

FIGS. 6 and 7 depict an alternative syringe de-capper 600 in accordance with the present disclosure. The syringe de-capper 600 includes a base 602, a de-capping member 604, and a suction cup 606 (shown in exploded view of FIG. 7). As shown, the suction cup 606 is disposed centrally on the bottom of the base 602. The de-capping member 604 is disposed extending from a top surface and toward a peripheral edge of the base 602. Other positions and configurations are possible.

The base 602 of the syringe de-capper 600 in FIGS. 6 and 7 is generally cylindrical. In other examples, the base 602 can be rectangular, triangular, or any other shape. The base 602 includes a sidewall 612, a top surface 614, and a bottom surface 616. Additionally, the base 602 can be designed for comfortable handheld movement. For example, the base 602 can have a height between approximately 0.25 inches and approximately 1.5 inches. Additionally, the diameter of the cylindrical base 602 can be between approximately 0.5 inches and approximately 6 inches. Based on the size and shape, the syringe de-capper 600 is easily held and moved in one hand. Additionally, though not illustrated in FIGS. 6 and 7, the bottom surface of the base 102 can include a recessed portion for receiving the suction cup 606.

As mentioned, the syringe de-capper 600 includes a de-capping member 604. The de-capping member 604 is integrally formed with the base 602, but in some examples the de-capping member 604 can be separate from and operatively attached to the base 602. Similar to the de-capping member 104 described in FIGS. 1-5, the de-capping member 604 includes an edge 620 disposed between a first surface 622 and a second surface 624. The edge 620 is disposed at a distal end of the de-capping member 604, relative the base 602. Additionally, as shown, the first surface 622 and second surface 624 diverge from the edge 620 to form a generally wedge-shaped de-capping member 604. The edge 620 can be a flat surface, a sharp or dull pointed edge, a partially rounded surface, or any other suitable shape and configuration. For example, the edge 620 can include a quarter circle or semicircle with a radius between approximately 0.02 inches and approximately 0.1 inches. The general shape and configuration of the de-capping member in FIGS. 6 and 7 can include any of the features described above with reference to FIGS. 1-5, as suitable and appropriate.

As shown, the generally wedge-shaped de-capping member 604 includes a proximal end 628a that is thicker than the distal end 628b, e.g., the edge 620. In some examples, the proximal end 628a, or a base of the de-capping member, has a thickness of between approximately 0.5 inches and approximately 1.25 inches. Additionally, the edge 620 can have a thickness of approximately 0.02 inches to approximately 0.1 inches. In some examples, the thickness of the de-capping member at the base is greater in magnitude than the length of the syringe needle. The base 602 has a base footprint 629a and the de-capping member 604 has a de-capping footprint 629b. As shown, the base footprint 629a is larger than the de-capping footprint 629b, however in some examples, the de-capping footprint 629b is the same as the base footprint 629a.

The de-capping member 604 additionally includes a slot 630. The de-capping member 604 of the present example includes only one slot 630. The disclosed version includes one slot 630, but in other versions, the de-capping member 104 can include more than one slot, similar to the de-capping member 104 of FIGS. 1-3. Slot 630 can define a width between approximately 0.15 inches and approximately 0.3 inches. But, in some examples, the width can be wider or narrower than shown in FIG. 6. The width of the slot 630 is configured to receive a needle, or needle hub of a syringe, but not receive the syringe barrel or the cap of the syringe.

Further, as mentioned, the syringe de-capper 600 includes the suction cup 606. As shown, the suction cup 606 includes a lever 642 configured to actuate the suction cup 606. The suction cup 606 is centrally disposed on the bottom surface 616 of the base 602. As can be seen in FIG. 7, the suction cup 606 includes an actuation arm 644 disposed through an opening (not depicted) in the base 602 and mechanically coupled to both the suction cup 606 and the lever 642. The lever 642 is pivotably coupled with the actuation arm 644 between a first position (shown in FIG. 6), which is generally horizontal, and a second position, which is pivoted approximately 90 degrees from the first position into a generally vertical orientation. In the first position, the lever 642 actuates the suction cup 606, meaning it draws the central portion of the suction cup 606 upward to create suction against a solid anchoring surface such as a flat table top or work bench, for example. In some examples, the actuation arm 644 is rigid or semi-rigid. Actuation of the lever 642 includes pivoting the lever relative the actuation arm 644 and the base 602. The lever 642 includes a cam 646 that, in the first position (shown in FIG. 6), forcibly engages the top surface 616 of the base 602 and draws the actuation arm 644 and suction cup 606 up towards the top surface 614. When the suction cup 606 is pressed against a flat, relatively smooth surface when the lever 642 is thus actuated, the suction cup 606 will be coupled to the flat surface via vacuum pressure between the suction cup 606 and the surface. In order to release the suction cup 606, the lever 642 can be pivoted into the second position (not shown) which also rotates the cam 646. Rotation of the cam 646 reduces the forcible engagement with the top surface 614 of the base 602, thereby allowing the actuation arm 644 and central portion of the suction cup 606 to move down and decouple from the flat surface.

In some examples, the base 602 additionally includes a slot 648, as shown in FIG. 6. The slot 648 can receive at least a portion the lever 642 when the lever 642 is disposed in the first position. As a result, the lever 642 is partially disposed within the base 602 in the first position for concealing the lever and preventing inadvertent decoupling from the flat surface below. Moreover, this concealment prevent the lever 642 from interfering with the use of the de-capping member 604.

While the syringe de-capper 600 in FIGS. 6 and 7 includes a suction cup 606, in other examples the syringe de-capper 600 can include other mechanisms for attaching to the lower supporting surface such as a weight (similar to the syringe de-capper 100 of FIGS. 1-3), a magnet, a hook and loop fastener, re-usable adhesive, gel, etc.

Figure 8:
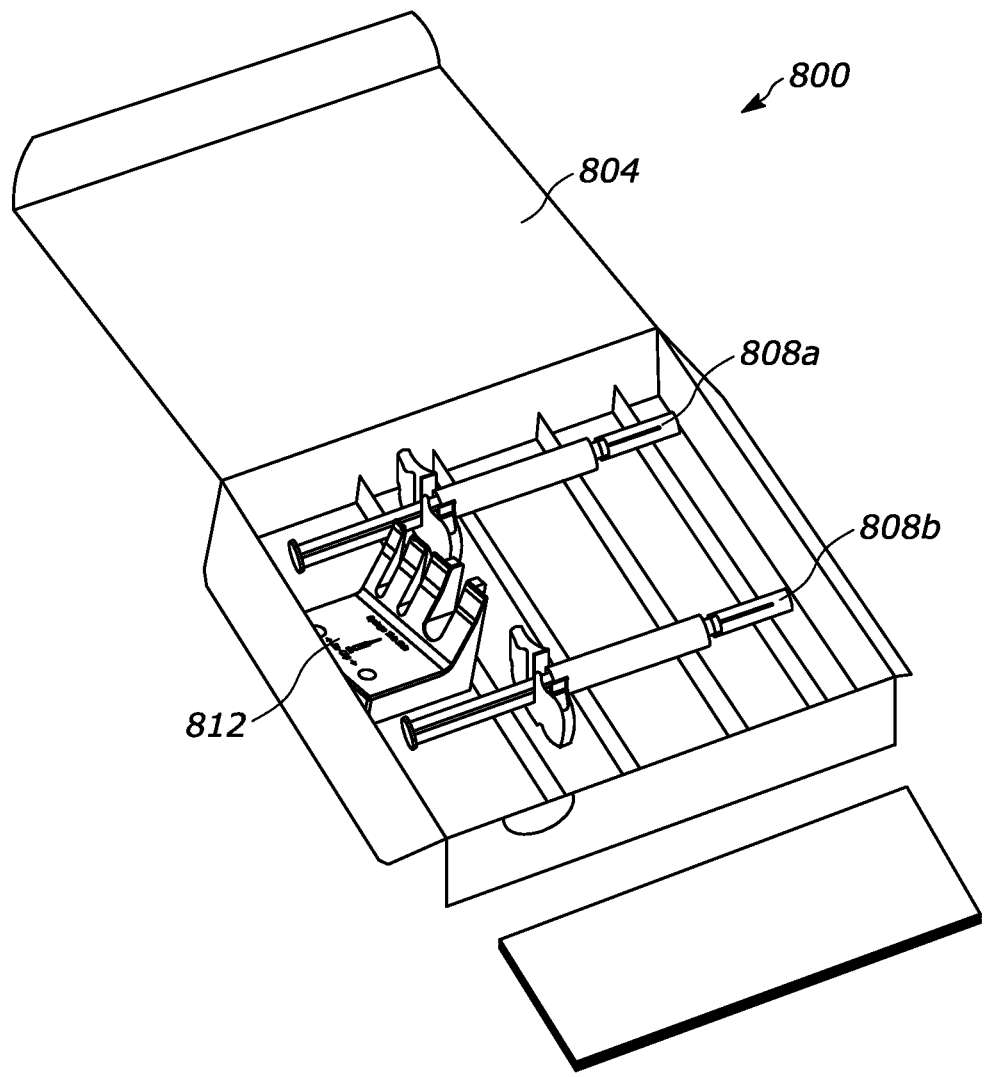
FIG. 8 is a perspective view of a syringe storage and de-capper kit.

FIG. 8 illustrates a syringe storage and de-capper kit 800. As shown, the syringe storage and de-capper kit 800 includes a storage container 804, a first syringe 808a, and a second syringe 808b, and a syringe de-capper 812 (not shown to scale). In some versions, either or both of the first syringe 808a or the second syringe 808b could include a pre-filled syringe. While FIG. 6 depicts two syringes, other versions of the kit could include one syringe or more than two syringes. In some examples, the syringe de-capper 812 of the storage and de-capper kit 800 includes a single slot 816, configured for the syringe stored in the sealed container 808. In some examples, the syringe de-capper 812 is substantially similar to the syringe de-capper 600 of FIGS. 6 and 7. Accordingly, an end user of either the first syringe 808a or the second syringe 808b can place the syringe de-capper on a table and de-cap the syringe with only one hand and without unneeded hand strength and hand dexterity.

In some examples, the first and second syringes 808a, 808b, are stored in individual containers (not shown), which could in some versions be sealed containers. For example, the first and second syringes 808a, 808b can be stored in blister packs having an inner cavity for storing a syringe. In some versions, the inner cavity could be sterile. For example, the contents of the individual containers can be sterilized before the container 808 is closed and stored in the storage container 804.

Additionally, as shown in FIG. 8, the storage container 804 is a box including a base 820, sidewalls 822a, 822b, 822c, and 822d, and a lid 824. The storage container 804 further includes ribs 830 to secure the first syringe 808a and the second syringe 808b. In other examples, the storage container 804 can include alternative syringe storage features to store syringes within the storage container 804. Further, the storage container 804 can be larger or smaller to accommodate more or fewer syringes, respectively.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing di merization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™ Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) molecules such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF a monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl)ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a KRAS$^{G12C}$ small molecule inhibitor, or another product containing a KRAS$^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)×anti-CD3 BiTE® (bispecific T cell engager) construct. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1 (PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed:

1. A syringe de-capper, comprising:
a base having a lower surface and an upper surface opposite the lower surface;
a de-capping member extending from the upper surface of the base, the de-capping feature including a proximal end adjacent to the base, a distal end spaced away from the base, and opposing first and second lateral surfaces defining a proximal thickness at the proximal end and a distal thickness at the distal end, wherein the distal thickness is smaller than the proximal thickness; and
a slot disposed in the de-capping member, the slot extending from the distal end of the de-capping member toward the proximal end of the de-capping member and configured to slidably receive a distal end of a syringe for removing a cap therefrom.

2. The syringe de-capper of claim 1, wherein the de-capping member includes an edge at the distal end from where the first and second surfaces diverge.

3. The syringe de-capper of claim 2, further including a recess disposed in the edge of the de-capping member and adjacent the at least one vertical slot.

4. The syringe de-capper of claim 3, wherein the edge has a first thickness and the recess disposed in the edge reduces the thickness of the edge from a first thickness to a second thickness.

5. The syringe de-capper of claim 1, further including at least one of (a) through (c):
(a) an aperture disposed in the upper surface of the base and being configured to receive the cap of the syringe,
(b) a suction cup coupled to the lower surface of the base,
(c) a weight disposed in the base.

6. The syringe de-capper of claim 1, wherein the second surface of the de-capping member is disposed approximately perpendicular to the upper surface of the base, and the first surface of the de-capping member is disposed at an angle relative to the first surface, the angle being greater than 0 degrees.

7. The syringe de-capper of claim 6, wherein the angle is in a range of approximately 5 degrees and approximately 45 degrees.

8. The syringe de-capper of claim 1, wherein the de-capping member includes a first wall portion on the first lateral surface having a first angle and a second wall portion on the first lateral surface having a second angle different from the first angle, the second wall portion adjacent the first wall portion.

9. The syringe de-capper of claim 1, wherein the slot has a width in a range between approximately 0.15 inches and approximately 0.3 inches.

10. The syringe de-capper of claim 1, further comprising a second slot disposed in the de-capping member, the second slot extending from the distal end of the de-capping member toward the proximal end of the de-capping member and configured to slidably receive a distal end of a syringe for removing a cap therefrom, wherein the slot has a first width and the second slot has a second width different from the first width.

11. The syringe de-capper of claim 10, wherein the second slot has a width in a range between approximately 0.35 inches and approximately 0.65 inches.

12. The syringe de-capper of claim 10, wherein the second slot disposed in the de-capping member additionally includes a rib on each side of the second slot such that a thickness of the de-capping member is greater adjacent the second slot than the first slot.

13. The syringe de-capper of claim 10, further comprising a third slot disposed in the de-capping member.

14. The syringe de-capper of claim 1, wherein at least one of (a) through (c):
(a) the base and the de-capping member are integrally formed as one piece,
(b) the base has a base footprint, and the de-capping member has a de-capping footprint, the base footprint being larger than the de-capping footprint,
(c) the de-capping feature is wedge shaped.

15. A syringe storage and de-capper kit, comprising:
a container having an interior cavity and a removable lid;
a syringe disposed within the container having a removable cap disposed over a needle extending from a distal end of the syringe; and
a syringe de-capper configured to de-cap the syringe, including a de-capping member extending from a base, the de-capping member including a proximal end adjacent to the base, a distal end spaced away from the base, and opposing first and second lateral surfaces defining a proximal thickness at the proximal end and a distal thickness at the distal end, wherein the distal thickness is smaller than the proximal thickness.

16. The syringe storage and de-capper kit of claim 15, further including a storage container, in which the container and the syringe de-capper are stored.

17. The syringe storage and de-capper kit of claim 15, wherein the syringe de-capper includes a slot to receive a distal end of the pre-filled syringe.

18. The syringe storage and de-capper kit of claim 17, wherein the slot has a smaller width than the removable cap.

19. The syringe storage and de-capper kit of claim 17, wherein the slot has a width in a range between approximately 0.2 inches and approximately 0.6 inches.

20. The syringe storage and de-capper kit of claim 15, wherein at least one of (a) through (e):
(a) the syringe de-capper includes a suction cup disposed on the base of the syringe de-capper,.
(b) the syringe de-capper includes a weight disposed in the base of the syringe de-capper,
(c) the base is integral with the syringe de-capper,
(d) the interior cavity, pre-filled syringe, and syringe de-capper are sterile when stored in the container,
(e) the first lateral surface includes a first wall portion having a first angle and a second wall portion having a second angle different from the first angle, the second wall portion adjacent the first wall portion.

* * * * *

UNITED STATES PATENT AND TRADEMARK OFFICE
CERTIFICATE OF CORRECTION

| | | |
|---|---|---|
| PATENT NO. | : 11,771,844 B2 | Page 1 of 1 |
| APPLICATION NO. | : 17/685433 | |
| DATED | : October 3, 2023 | |
| INVENTOR(S) | : Jeffrey C. Yeary | |

It is certified that error appears in the above-identified patent and that said Letters Patent is hereby corrected as shown below:

In the Claims

Column 16, Line 48, Claim 20, "de-capper,." should be -- de-capper, --.

Signed and Sealed this
Fifth Day of November, 2024

*Katherine Kelly Vidal*

Katherine Kelly Vidal
*Director of the United States Patent and Trademark Office*